(12) United States Patent
Henke et al.

(10) Patent No.: US 12,303,306 B2
(45) Date of Patent: May 20, 2025

(54) MODULARLY STRUCTURED LID FOR A STERILE CONTAINER AND FILTER COVERING FOR SUCH A LID

(71) Applicant: Aesculap AG, Tuttlingen (DE)

(72) Inventors: Matthias Henke, Fridingen (DE); Andreas Elisch, Rottweil (DE); Matthias Schweizer, Tuttlingen (DE); Stefan Thomas, Tuttlingen (DE); John Gray-Dreizler, Niedereschach (DE); Philipp Bohnenstengel, Steisslingen (DE); Thomas Sterk, Singen (DE); Betina Bernauer, Geisingen (DE)

(73) Assignee: Aesculap AG, Tuttlingen (DE)

( * ) Notice: Subject to any disclaimer, the term of this patent is extended or adjusted under 35 U.S.C. 154(b) by 141 days.

(21) Appl. No.: 17/950,901

(22) Filed: Sep. 22, 2022

(65) Prior Publication Data

US 2023/0025190 A1 Jan. 26, 2023

Related U.S. Application Data

(62) Division of application No. 16/636,107, filed as application No. PCT/EP2018/070732 on Jul. 31, 2018, now Pat. No. 11,490,982.

(30) Foreign Application Priority Data

Aug. 3, 2017 (DE) .................... 10 2017 117 624.1

(51) Int. Cl.
*A61B 50/30* (2016.01)
*A61B 50/00* (2016.01)
*A61L 2/26* (2006.01)

(52) U.S. Cl.
CPC .............. *A61B 50/30* (2016.02); *A61L 2/26* (2013.01); *A61B 2050/007* (2016.02); *A61L 2202/182* (2013.01); *A61L 2202/24* (2013.01)

(58) Field of Classification Search
CPC ..... A61B 50/30; A61B 2050/007; A61L 2/26; A61L 2202/182; A61L 2202/24
(Continued)

(56) References Cited

U.S. PATENT DOCUMENTS 1,316,818 A * 9/1919 Sweet .................... B65D 9/32
292/87
1,468,208 A * 9/1923 Mueller ................. B65D 53/06
215/233
(Continued)

FOREIGN PATENT DOCUMENTS

DE          10156937 A1    6/2003
DE       102004020803 A1   11/2005
(Continued)

OTHER PUBLICATIONS

Translation of EP 2,179,746 provided by Espacenet. (Year: 2024).*
(Continued)

*Primary Examiner* — James N Smalley
(74) *Attorney, Agent, or Firm* — Christopher A. Rothe; CM Law

(57) ABSTRACT

A filter covering for a sterile container lid, for completely covering at least one gas exchange portion, which is provided on a lid component of the sterile container lid, on an outside of the sterile container lid, the filter covering having at least two clip portions arranged opposite to each other on the filter covering, which are adapted to engage in a form-fitting manner in at least two clip receiving portions provided on the lid component, and by which the filter covering is mountable to and dismountable from the lid component without tools.

20 Claims, 2 Drawing Sheets

(58) Field of Classification Search
USPC .............. 220/326, 784, 845, 847; 215/287; 24/462
See application file for complete search history.

(56) References Cited

U.S. PATENT DOCUMENTS

| | | | | |
|---|---|---|---|---|
| 2,963,761 | A * | 12/1960 | Haydock | A47B 3/12 248/689 |
| 2,979,554 | A * | 4/1961 | Maitland | H05K 7/12 439/82 |
| 3,324,853 | A * | 6/1967 | Czorny | A61M 5/3216 604/162 |
| 3,370,815 | A * | 2/1968 | Opperthauser | F16L 55/035 248/74.2 |
| 3,544,146 | A * | 12/1970 | Asenbauer | B65D 45/18 292/87 |
| D248,347 | S * | 7/1978 | McCollum | D6/552 |
| 4,452,373 | A * | 6/1984 | Pearce | A45C 11/24 220/829 |
| D279,959 | S * | 8/1985 | Nimmo | D8/382 |
| 4,556,150 | A * | 12/1985 | Ikumi | F16B 5/0064 220/326 |
| 4,560,083 | A * | 12/1985 | Danico | B62D 25/24 220/795 |
| 4,585,036 | A * | 4/1986 | Jartoux | F16G 11/103 138/172 |
| 4,915,913 | A | 4/1990 | Williams et al. | |
| 5,080,874 | A | 1/1992 | Nichols | |
| 5,524,755 | A | 6/1996 | Deeds | |
| 5,755,484 | A * | 5/1998 | Chou | B60J 5/0447 296/146.7 |
| 5,921,422 | A * | 7/1999 | Hunter | H05K 5/0013 220/326 |
| 6,585,942 | B1 | 7/2003 | Bussell et al. | |
| D478,738 | S * | 8/2003 | Workman | D6/552 |
| 6,715,628 | B1 | 4/2004 | Nichols et al. | |
| 7,316,506 | B2 * | 1/2008 | Deonarine | G01K 11/06 374/E11.006 |
| 7,381,385 | B2 | 6/2008 | Gleichauf et al. | |
| 7,595,032 | B2 * | 9/2009 | Banks | A61L 2/26 220/372 |
| D691,032 | S * | 10/2013 | Chen | D8/396 |
| 8,662,455 | B2 * | 3/2014 | Hernandez | F16B 2/245 248/222.12 |
| 9,005,541 | B2 | 4/2015 | Kreidler | |
| 2004/0256269 | A1 | 12/2004 | Gleichauf et al. | |
| 2006/0076081 | A1 | 4/2006 | Gleichauf et al. | |
| 2007/0084862 | A1 | 4/2007 | Jakab et al. | |
| 2012/0189508 | A1 | 7/2012 | Kreidler | |
| 2015/0053703 | A1 | 2/2015 | Kreidler et al. | |

FOREIGN PATENT DOCUMENTS

| | | |
|---|---|---|
| DE | 102004020805 B3 | 1/2006 |
| DE | 102008053301 A1 | 4/2010 |
| DE | 202011001772 U1 | 4/2011 |
| DE | 202013007581 U1 | 9/2013 |
| EP | 2179746 A1 | 4/2010 |
| WO | 03041604 A1 | 5/2003 |

OTHER PUBLICATIONS

Office Action received in German Application No. 10 2017 117 624.1, dated Jun. 8, 2020, with translation, 11 pages.
Search Report and Written Opinion received in International Application No. PCT/EP2018/070732, dated Nov. 12, 2018, 8 pages.
Search Report received in German Application No. 10 2017 117 624.1, dated Apr. 10, 2018, with translation, 11 pages.

* cited by examiner

MODULARLY STRUCTURED LID FOR A STERILE CONTAINER AND FILTER COVERING FOR SUCH A LID

CROSS REFERENCE TO RELATED APPLICATIONS

This application is a divisional of U.S. application Ser. No. 16/636,107, filed Feb. 3, 2020, which is the United States national stage entry of International Application No. PCT/EP2018/070732, filed Jul. 31, 2018, and which claims the benefit of priority of German Application No. 10 2017 117 624.1, filed Aug. 3, 2017. The contents of U.S. application Ser. No. 16/636,107, International Application No. PCT/EP2018/070732, and German Application No. 10 2017 117 624.1 are incorporated by reference herein in their entireties.

FIELD

The invention relates to a modularly structured lid for a sterile container, to a sterile container having such lid and to a filter covering for such lid.

BACKGROUND

Sterile containers are basically known from prior art and have been in use in medicine especially for sterilizing surgical instruments, implants and the like and for temporarily storing and, resp., transporting the same after sterilization. Objects to be sterilized in general are initially inserted into the sterile container or, resp., into a trough-shaped first container part of the sterile container. Subsequently, a lid-shaped second container part or a lid is disposed at or, resp., on the trough-shaped first container part and the two container parts are closed relative to each other. The closed sterile container is supplied to a sterilizer. Therein the objects to be sterilized provided in the interior of the container are sterilized in any sterilization process (e.g. hot air sterilization, steam sterilization etc.).

It is known from prior art to equip sterile containers with filter units/filters which are intended to prevent germs, bacteria or the like from penetrating the sterile container and to enable sterile fluid exchange during sterilization. The filter units frequently can be mounted and dismounted from an inner side of the sterile container/from inside and are disposed at an inner side of the lid on a gas exchange portion of the lid which is especially perforated. At an outer side of the lid, the gas exchange portion is covered by an external cover/filter covering which serves for protecting the filter device against mechanical influences, for example during transport or storage.

In the sterile container lids known from prior art, the filter coverings are basically mounted ex works already on lid components of the sterile container lid. Said known integral solutions for a sterile container lid frequently are difficult to handle for a user, especially as the filter covering cannot be easily removed from the lid component and a user cannot inspect/view the filter from outside. Filter units mounted from inside therefore are inspected for possible damage only after the sterilized objects have been removed by a sterile user. If it is found that the filter unit is damaged or is not present at all, the removed objects must be sterilized again, a possibly contaminated instrument bench on which the removed objects have been placed in the meantime, must be cleaned and the sterile user must change clothes, where necessary.

SUMMARY

Against this background, it is the object of the present invention to avoid or at least alleviate the afore-mentioned drawbacks from prior art. In particular, a sterile container and, resp., a sterile container lid shall be provided which a user can handle more easily and which facilitates inspection of a filter unit/filter without previous opening of the sterile container.

To begin with, the invention relates to a modularly structured lid for a sterile container or, resp., of a sterile container comprising: a lid component which has at least one gas exchange portion, which is in particular perforated, on which on the inner side of the lid at least one filter device can be/is arranged, and at least one filter covering which is preferably (at least partially) transparent and which (completely) covers the at least one gas exchange portion on an outside of the lid and, resp., by means of which the at least one gas exchange portion can be (completely) covered, wherein the lid component has at least one, especially standardized, clip receiving portion and the filter covering has at least one, especially standardized, clip portion (or vice versa) by means of which the filter covering and the cover component can be interlocked to each other, in particular by clipping, and can be mounted and removed without tools.

A central aspect of the present invention is the modular structure of the lid. In accordance with the invention, the lid component and the filter covering constitute two separate components which can be made available to a user both in a mounted condition and in a dismounted/separate condition. The lid component preferably is a component that is adapted to completely cover and close a trough-shaped container part of a sterile container. The filter covering/external covering serves for protecting the filter device, which may be, for example, a filter, filter element, combination of filter holder and filter element etc., against mechanical influences (e.g. pointed/sharp-edged objects which may pierce or cut the filter) and prevents/reduces penetration of liquids into the sterile container. The filter device preferably can be arranged at an inner side of the lid/of the sterile container on a gas exchange portion of the lid component and completely covers said gas exchange portion which, further preferred, has a plurality of perforations/holes so that gas exchange between an inner side of the sterile container/lid and an outer side of the sterile container/lid can (exclusively) take place via the filter device. When the filter covering is mounted on the lid component, the gas exchange portion is preferably completely (over its entire surface) covered by the filter covering.

Further preferred, the lid component has at least one, preferably two, standardized receiver(s)/at least one, preferably two, standardized clip receiving portion(s) which is/are suited to positively receive therein filter coverings having different characteristics, each of which includes at least one, preferably two, standardized engaging portion(s)/at least one, preferably two, standardized clip portion(s). For example, different filter coverings that differ as to material or cost, as to their mechanical properties, leak properties and as to their preferred intended use (e.g. different sterilization processes) can be made available to a user. The various filter coverings optionally can be exchanged, according to the invention, so that a filter covering adapted in its properties to the respective field of application can be used.

The fact that the filter covering and the lid component can be (positively) interlocked to each other and can be mounted and removed without tools/without the use of tools allows to achieve easy handling and any retrofitting by further developed filter coverings. Moreover, after completed sterilization the filter covering can be easily removed manually from the lid component and a condition of the filter device can be inspected by a user without the user having to open the sterile container. For example, the user can see whether the filter device is inserted and is possibly damaged, or if a process indicator is attached to the filter device, can check whether the filter device has been subjected to a process similar to sterilization. Of preference, the filter covering is therefore removed after each sterilizing operation and is re-mounted, which is also accompanied by improved cleaning of both the lid component and the filter covering.

The filter covering may preferably be made in one piece (at least partially) from transparent plastic material, preferably by injection molding. This offers the further advantage that a user can view the filter device even when the filter covering is mounted on the lid component. In addition, the filter covering is thus realized at low cost as well as for simple handling and manufacture.

Basically, a generic lid component of a sterile container (such as of the present sterile container according to the invention) has, as already described before, a substantially flat/planar upper side/outside of the lid (hereinafter also referred to as lid component main plane) which is surrounded by a frame usually/optionally preferably (adhesively) formed thereon by beading/deep-drawing, which frame can be dimensioned so that, when the lid component is attached to the trough-shaped container part, the frame encompasses the outer side of the edge of the through-shaped container part. Moreover, the gas exchange portion forming at the outside of the lid defines a plane which is raised/offset in height against the lid component main plane. The lid component main plane as well as the plane defined/spanned by the gas exchange portion are interconnected via a base/transition portion surrounding the gas exchange portion in frame shape, said base/transition portion being preferably formed integrally on the lid component main plane.

According to a preferred development of the invention, at the preferably standardized clip receiving portion of the lid component a recess or a shell-type handle recess/indentation (with respect to the lid component main plane) is provided at which the lid component, especially via recess/indentation side surfaces or flanks formed thereon, merges from the lid component main plane into a recess base area (possibly extending in parallel to the lid component main plane) which is offset against the lid component main plane by a first height downward (toward an inner side of the lid/of the sterile container) and via the transition portion being undercut/withdrawn or S-shaped at least in this area merges from the recess base area into the gas exchange portion which is offset against the lid component main plane (possibly equally in parallel), especially by a second height upward (toward an outer side of the lid/outer side of the sterile container) against the lid component main plane.

In other words, preferably at each of opposing sides of the gas exchange portion a shell-type handle or indentation is formed on the lid component main plane, the indentation edge of which facing the gas exchange portion forms a respective undercut (S-shaped cross-section) in which the preferably equally opposing clip portions of the filter covering (resiliently) interlock, when said undercut is placed on the gas exchange portion and, resp., the transition portion/base (such as in the form of a generally known keep-fresh pack with a lid). If the filter covering is to be removed again, in the area of the shell-type handles/indentations merely the lower edge area of the filter covering (facing the lid component main plane) has to be seized by the finger tips and the filter covering has to be removed elastically over the respective undercut.

Of preference, the (standardized) clip portion of the filter covering is in the form of a C-shaped/clamp-shaped side portion/end portion/strip of the filter covering and at the C-shaped side portion a laterally outwardly projecting grip portion is arranged which is manually operable when mounting and dismounting the filter covering on the lid component due to the shell-type handle/indentation formed in this area, as already described in the foregoing.

The clip portion is preferably formed at a side/end/edge portion of the filter covering as a portion bent away in clamp shape/C shape from an upper side of the filter covering (hereinafter also referred to as filter covering main plane). In other words, the filter covering is laterally delimited at least in portions by the clip portion on at least one side/edge/end. The grip portion extends preferably in parallel to the filter covering main plane outward away from the clip portion.

When the filter covering is mounted on the lid component, it is of advantage when the clamp-shaped side portion/end portion of the filter covering which forms the clip portion engages in or is clipped in the undercut transition portion of the clip receiving portion of the lid component, as equally already indicated in the foregoing.

Clipping the filter covering onto/into the lid component provides, especially when the clip portion and the grip portion of the filter covering are disposed/provided on a side/edge/end of the filter covering, a suitable mechanical connection by which the filter covering and the lid component can be interlocked with each other and can be mounted and removed without tools.

In other words, the clip portion is preferred to be a clamp-shaped side portion/end portion of the filter covering and the clip receiving portion is preferred to have an undercut portion, wherein when the filter covering is mounted on the lid component the clamp-shaped side portion of the filter covering engages in/is clipped into the undercut portion of the clip receiving portion.

One advantageous example embodiment provides for the filter covering to include two clip portions which are disposed on opposite, preferably parallel, sides and/or ends of the filter covering and for the lid component to include two clip receiving portions which are disposed on opposite, preferably parallel, sides and/or ends of the gas exchange portion and, when the filter covering is mounted on the lid component, for the two clip portions to engage in/be clipped into the two clip receiving portions.

When mounting the filter covering on the lid component, preferably at first the first clip portion is inserted into the first clip receiving portion. Subsequently, the second clip portion is pressed into the second clip receiving portion by manually operating the grip portion while the filter covering is reversibly elastically bent open. When the filter covering is dismounted from the lid component, the filter covering is pressed downwards at a central portion thereof and is pulled at one of the two grip portions, thus causing the filter covering to be reversibly elastically bent open and to be removed from the lid component.

Especially preferred, the filter covering is made from amorphous thermoplastic and is transparent and enables the filter device to be visually inspected from the outside of the lid without previous dismounting of the filter covering from the lid component.

When the filter covering is transparent, a condition thereof can be inspected by a user without the filter covering having to be dismounted from the lid component. For example, the user can see whether the filter device is inserted, is possibly damaged, or can check, if a process indicator has been applied to the filter device, whether the filter device has been subjected to a process similar to sterilization. When the filter covering is further made from amorphous thermoplastic, on the one hand the elasticity of the filter covering required for mounting and dismounting is provided along with sufficient stiffness and strength (for fastening the filter covering to the lid component), on the other hand the entire filter covering is enabled to be manufactured at low cost in one piece by injection molding.

Moreover, the invention relates to a sterile container having a trough-shaped container portion and a lid as afore-described.

In addition, the invention relates to a filter covering for a sterile container lid, especially for a lid as afore-described, for completely covering at least one gas exchange portion, which is especially perforated and is provided on a lid component of the sterile container lid, at an outside of the lid which is integrally made from, preferably transparent, plastic material and includes at least one, especially standardized, clip portion, preferably two standardized clip portions, which is/are adapted to be interlocked, especially by clipping, to an, especially standardized, clip receiving portion provided on the lid component and by means of which the filter covering can be mounted and dismounted on the lid component without using tools.

Of preference, the clip portion is in the form of a C-shaped/clamp-shaped side portion/end portion of the filter covering and, on the C-shaped side portion, a laterally outwardly projecting grip portion is arranged which is manually operable for mounting and dismounting the filter covering on the lid component.

Further, the filter covering preferably includes two clip portions which are disposed on opposite, preferably parallel sides and/or ends of the filter covering and are adapted to positively engage in two clip receiving portions disposed on opposite, preferably parallel, sides and/or ends of the gas exchange portion, when the filter covering is mounted on the lid component.

Advantageously, the filter covering is further made from amorphous thermoplastic and is transparent and enables a filter device which can be arranged on an inner side of the lid of the gas exchange portion to be visually inspected from an outer side of the lid without previous dismounting of the filter covering from the lid component.

BRIEF DESCRIPTION OF THE DRAWING FIGURES

Hereinafter, the invention shall be illustrated in detail by way of figures, wherein.

The figures are merely schematic and serve exclusively for the comprehension of the invention. Like elements are provided with like reference numerals.

DETAILED DESCRIPTION

Figure 1:
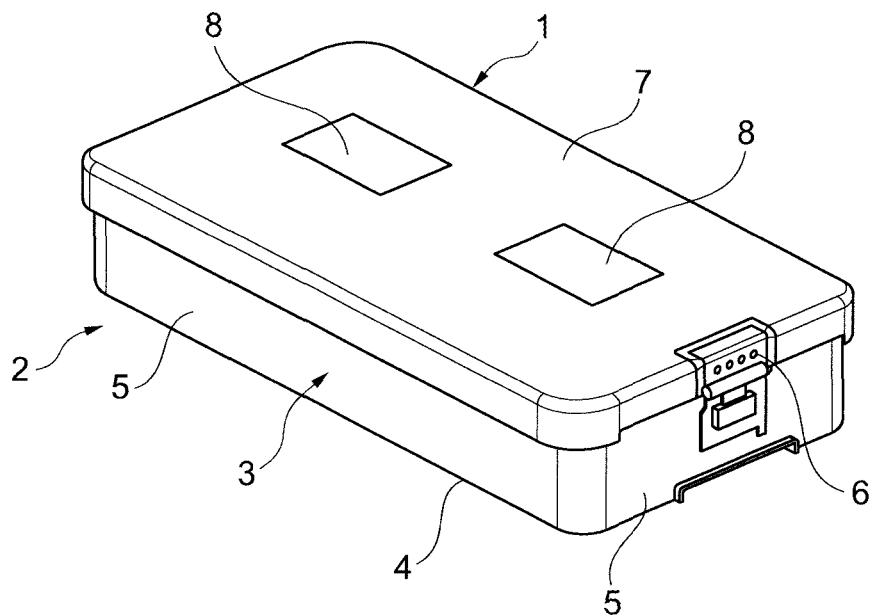
FIG. 1 shows a perspective view of a sterile container having a lid and a receiving container.

FIG. 1 illustrates a perspective view of a lid 1 according to the invention for a sterile container 2 which closes a trough-shaped receiving container 3. The receiving container 3 comprises a container bottom 4 and container walls 5 rising from said container bottom. The receiving container 3 and the lid 1 are closed by means of a closure 6. The lid 1 includes a lid component 7 covered on the outside by two filter coverings 8. According to the invention, also one filter covering 8 (one gas exchange portion on the lid component 7) or more than two filter coverings 8 (more than two gas exchange portions on the lid component 7) may be provided. Beneath the filter coverings 8, portions that are perforated or are in the form of a perforated plate (not shown) are provided on the lid component 7 in FIG. 1. The lid component 7 completely covers the receiving container 3. The lid component 7 and the filter covering 8 are separate components.

Figure 2:
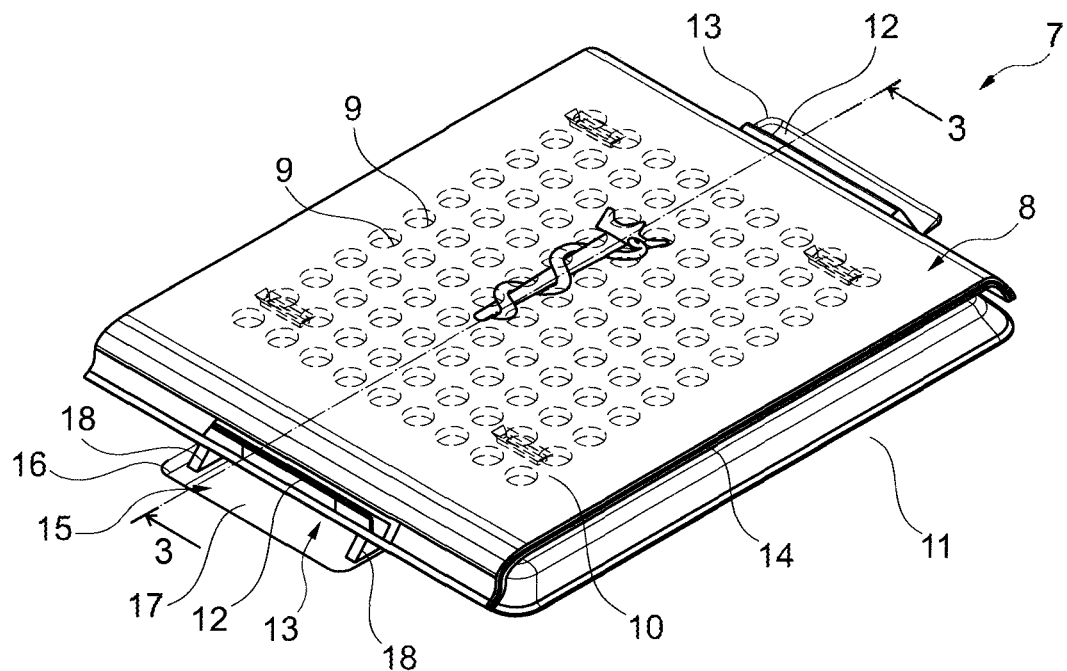
FIG. 2 shows an enlarged perspective view of a filter covering arranged on a lid component.

FIG. 2 illustrates an enlarged perspective view of a filter covering 8 arranged on the lid component 7. The filter covering 8 shown in FIG. 2 is transparent/translucent and is made, for example, from amorphous plastic/thermoplastic by injection molding. Due to the transparency of the filter covering 8, perforations/holes 9 provided on a gas exchange portion 10 of the lid component 7 are visible. The perforations/holes 9 of the gas exchange portion 10 permit fluid exchange during sterilization. It is already evident from FIG. 2 that the gas exchange portion 10 is a portion protruding from a lid component main plane 11. The filter covering 8 is rectangular and plate-shaped or disk-shaped (in the form of a thin plate/disk). In particular, a height/thickness of the filter covering 10 is negligible in relation to its length and width.

At each of two opposing, preferably shorter, sides (of the rectangle) the filter covering 8 has a clip portion 12 which is provided on a central portion of the respective side (of the rectangle). Each of the clip portions 12 of the filter covering 8 is positively received in clip receiving portions 13 of the lid component 7. On the (rectangular) sides of the filter covering 8 including the clip portions 12, the filter covering is bent and in portions abuts on the projecting gas exchange portion 10 of the lid component and at the end side abuts on the lid component main plane 11. At the two further, equally opposing and preferably longer sides (of the rectangle) the filter covering 8 is arranged to be spaced apart from the gas exchange portion 10, especially by about 2 mm. During sterilization, fluid exchange may take place especially via the narrow gap 14 provided between the filter covering 8 and the gas exchange portion 10.

Each clip receiving portion 13 has, inter alia, a recess 15 which is composed of recess side surfaces 16 and a recess base area 17. Projections 18 of the filter covering 8 are guided at two opposing recess side surfaces 16. In other words, the projections 18 of the filter covering 8 are arranged adjacent to the two opposing recess side surfaces 16, when the filter covering 8 is mounted on the lid component 7.

Figure 3:
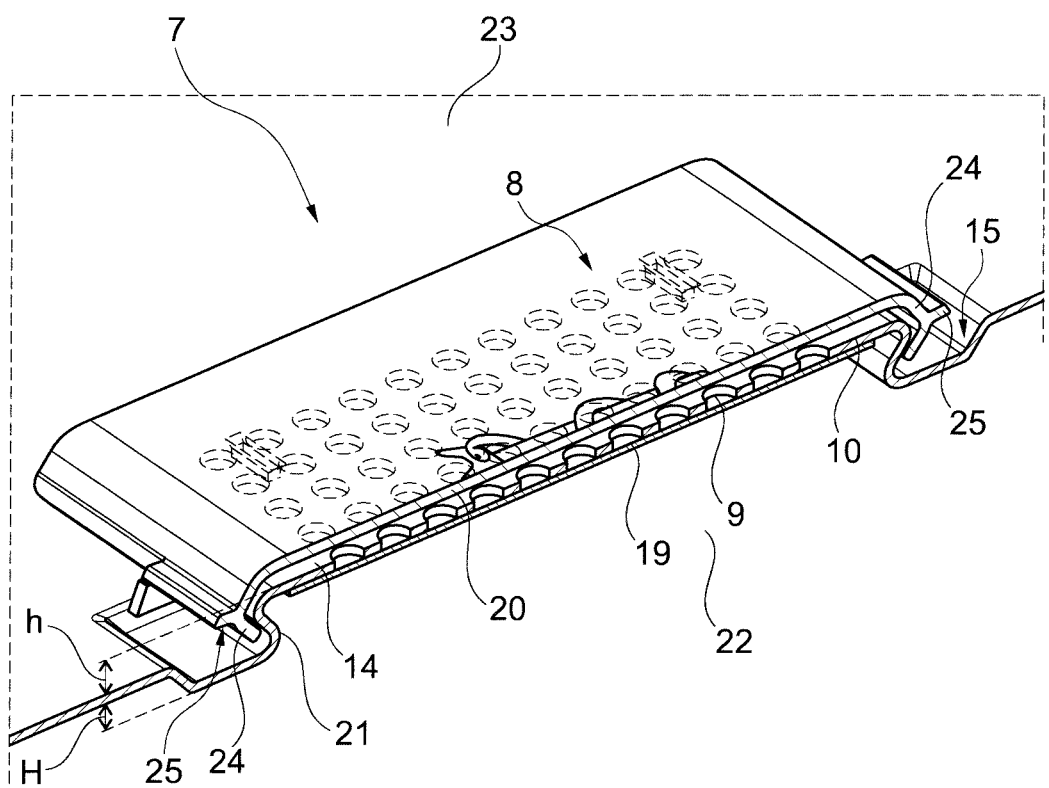
FIG. 3 shows a perspective view cut along the axis 3-3 in FIG. 2 of the filter covering arranged on the lid component.

FIG. 3 illustrates a perspective view cut along the axis 3-3 in FIG. 2 of the filter covering 8 disposed on the lid component 7. Here it is first of all evident that, on a lower side/toward an inner side of the lid/an inner side of the sterile container of the gas exchange portion 10 having the holes/perforations 9, a filter 19 which is a rectangular thin filter element and completely covers all holes/perforations 9 of the gas exchange portion is arranged. Further, is becomes more apparent from FIG. 3 that the filter covering 8 and the gas exchange portion 10 are spaced apart from each other or, in other words, a gap 14 is defined between the gas exchange portion 10 and a filter covering main plane 20.

It is further apparent from FIG. 3 that, adjacent to the recess side faces 16 and the recess base area 17, the recess 15 has an S-shaped transition portion 21. In other words, at the recess 15 the lid component 7 merges, via recess side surfaces 16, from the lid component main plane 11 into the recess base area 17 and merges, via the S-shaped transition portion 21, from the recess base area 17 into the gas exchange portion 10. The recess base area 17 is offset against the lid component main plane 11 by a height H downwards/toward an inner side of the lid 22. The gas exchange portion 10 is offset against the lid component main plane 11 by a height h upwards/toward an outside of the lid 23. The recess base area 17, the lid component main plane 11 and the gas exchange portion 10 are parallel to one another. The S-shaped transition portion 21 extends in S shape between the recess base area 17 and the gas exchange portion 10.

Moreover, it is evident from FIG. 3 in which way the clip portions 12 of the filter covering 8 are configured. The clip portions 12 are clamp-shaped/C-shaped end portions/(rectangular) side portions 24 which extend at two opposite (rectangular) sides of the filter covering downwards/toward an inner side of the lid 22 from the filter covering main plane 20 in clamp shape/C shape. A grip portion 25 extends to protrude laterally outwards from the clamp-shaped/C-shaped (rectangular) side portions 24. The grip portion 25 is in parallel to the filter covering main plane 20.

When the filter covering 8 is mounted on the lid component 7, the clamp-shaped/C-shaped (rectangular) side portions 24 of the filter covering 8 are clipped onto the S-shaped transition portions 21 of the lid component 7 or, resp., the C-shaped (rectangular) side portions 24 cling to the S-shaped transition portions 21 so that the filter covering 8 and the lid component 7 are thus interlocked with each other. Clipping of the clip portions 12 of the filter covering 8 onto/into the clip receiving portions 13 of the lid component 7 is facilitated especially by the elasticity of the employed amorphous thermoplastic.

What is claimed:

1. A filter covering for a sterile container lid, for completely covering at least one gas exchange portion, which is provided on a lid component of the sterile container lid, on an outside of the sterile container lid, wherein the filter covering extends in a main plane, and the filter covering comprises:
   at least two clip portions arranged opposite to each other, and
   a plate having a height, a length extending in the main plane and a width extending in the main plane, wherein the height is less than the length and less than the width,
   wherein the at least two clip portions are formed as portions extending from the plate and bent away from the main plane, and each of the at least two clip portions comprises:
      a first end attached to the plate,
      a curved surface extending from the first end and defining a bracket-shape or a C-shape having a concave side and a convex side opposite the concave side, and
      a second end defining a terminal free edge of the curved surface,
   wherein in a sectional view of the filter covering viewed along the main plane in which the at least two clip portions are provided, an entire section of the plate extends in the main plane, and the at least two clip portions bend in a first direction away from the main plane such that the respective concave sides of the respective curved surfaces face one another, and the respective terminal free edges are located closer to each other than respective portions of the respective curved surfaces immediately adjacent to the respective terminal free edges,
   wherein a first clip portion of the at least two clip portions comprises a first grip portion projecting in a direction away from the plate, wherein the first grip portion extends from the respective convex side of the first clip portion at a location between and spaced from the respective first end and the respective terminal free end of the first clip portion, and
   wherein a second clip portion of the at least two clip portions comprises a second grip portion projecting in a direction away from the plate, wherein the second grip portion extends from the respective convex side of the second clip portion at a location between and spaced from the respective first end and the respective terminal free end of the second clip portion.

2. The filter covering according to claim 1, wherein the filter covering is made of a plastic material in one piece.

3. The filter covering according to claim 1, wherein the at least two clip portions are arranged on opposite sides and/or ends of the filter covering.

4. The filter covering according to claim 1, further comprising one or more supports extending from the plate in the first direction, between the respective first ends of the at least two clip portions, wherein the one or more supports are configured to space the plate from an adjacent surface when the at least two clip portions are positioned to hold the filter covering against the adjacent surface.

5. The filter covering according to claim 1, wherein the plate is rectangular.

6. The filter covering according to claim 1, wherein the at least two clip portions consist of exactly two clip portions.

7. The filter covering according to claim 1, wherein the filter covering is rectangular with a first side, a second side opposite the first side, a third side, and a fourth side opposite the third side, the at least two clip portions being provided on the first side and the second side.

8. The filter covering according to claim 7, wherein the at least two clip portions are not provided on the third side and the fourth side.

9. The filter covering according to claim 7, wherein the first side and the second side are shorter than the third side and the fourth side, respectively, and
   wherein the first side and the second side each comprise one of the at least two clip portions.

10. The filter covering according to claim 1, wherein the respective curved surface of the first clip portion extends parallel to the main plane through a respective first distance, the first grip portion extends parallel to the main plane from a respective first end to a respective second end through a respective second distance, and the respective second distance is less than the respective first distance.

11. The filter covering according to claim 10, wherein the respective curved surface of the second clip portion extends parallel to the main plane through a respective first distance, the second grip portion extends parallel to the main plane from a respective first end to a respective second end through a respective second distance, and the respective second distance is less than the respective first distance.

12. The filter covering according to claim 1, wherein the first grip portion and the second grip portion extend parallel to the main plane.

13. The filter covering according to claim 1, wherein the filter covering is made from amorphous thermoplastic and is transparent for visually inspecting a filter device arranged on a lid inner side of a gas exchange portion.

14. The filter covering according to claim 1, wherein the filter covering is at least partially transparent.

15. The filter covering according to claim 1, wherein the filter covering is an injection-molded part.

16. The filter covering according to claim 1, wherein the filter covering is elastically bendable.

17. The filter covering according to claim 1, wherein the respective terminal free edge of each clip portion is located at a greater distance from the main plane than any other part of the respective clip portion.

18. The filter covering according to claim 1, wherein a "C" is formed between each of said respective ends of the clip portions and the main plane in the sectional view.

19. The filter covering according to claim 1, wherein each of said respective curved surfaces immediately adjacent to the respective terminal free edges ends at a downward angle extending away from the main plane and towards an opposite one of the at least two clip portions.

20. The filter covering according to claim 1, wherein the plate extends in the main plane from a first edge at which a first one of the at least two clip portions is located to a second edge at which a second one of the at least two clip portions is located, and an entirety of the filter covering between the first edge and the second edge extends in the main plane.

\* \* \* \* \*